United States Patent [19]
Paulus et al.

[11] Patent Number: 5,847,190
[45] Date of Patent: Dec. 8, 1998

[54] DENDRITIC NITROGEN-CONTAINING ORGANIC COMPOUNDS CONTAINING PLANAR-CHIRAL OR AXIAL-CHIRAL END GROUPS AND THE PREPARATION AND USE THEREOF

[75] Inventors: Wolfgang Paulus, Mainz; Fritz Vögtle, Alfter-Impekoven; Jörg Issberner, Swisttal-Movenkoven, all of Germany

[73] Assignee: BASF Aktiengesellschaft, Ludwigshafen, Germany

[21] Appl. No.: 859,182

[22] Filed: May 20, 1997

[30] Foreign Application Priority Data

May 29, 1996 [DE] Germany .................. 19 621 510.2

[51] Int. Cl.[6] .................. C07C 251/24; C08G 73/02
[52] U.S. Cl. .................. 558/302; 558/308; 558/314; 558/315; 558/316; 260/350 R; 528/129; 528/145; 528/146; 528/266; 556/32; 502/200
[58] Field of Search .................. 558/302, 308, 558/314, 315, 316; 260/350 R; 528/129, 145, 146, 266; 556/32; 502/200

[56] References Cited

U.S. PATENT DOCUMENTS 4,631,337  12/1986  Tomalia et al. .................. 528/391

FOREIGN PATENT DOCUMENTS

93/14147   7/1993   WIPO .
93/19787  10/1993   WIPO .
96/15097   5/1996   WIPO .

OTHER PUBLICATIONS

Buhleier et al., Synthesis, 1978, pp. 137–139 (=pp. 155–158).
de Brabander–van den Berg et al., Agnew. Chem., 105, 1993, 1370–1372.
Agnew Chem. Int. Ed., 1993, 31, 1308–1311.
Woerner et al., Agnew. Chem., 105, 1993, 1367–1370.
Agnew Chem. Int. Ed. Engl., 32, 1993, 1306–1308.
Moors et al., Chem. Ber., 126, 1993, 2133–2135.
Issberner et al., Agnew. Chem., 106, 1994, 2507–2514.
Agnew. Chem. Int. Ed., 33, 1994, 2313–2320.
Mekelburger et al., Agnew. Chem., 104, 1992, 1609–1614.
Angew. Chem. Int. Ed., 31, 1992, 1571–1576.
Tomalia et al., Top Curr. Chem., 165, 1993, 193–313.
Jansen et al., Angew. Chem., 107, 1995, 1321–1324.
DuBois et al., Inorg. Chem., 33, 1994, 5482–5490.
De et al., Tetrah. Asymmetry, 6(9), 1995, 2105–2108.
Henrici–Olivé et al., Agnew. Chem., 86, 1974, 1–56.
Yamashita et al., Synlett, 1995, 829–830.
White et al., Synlett, 1995, 831–832.
Chang et al., J. Am. Chem. Soc., 116, 1994, 6937–6938.
Ganeshpure et al., Tetradedron Lett, 29, 1988, 6629–6632.
Chang et al., Tetradedron Lett, 35, 1994, 669–672.
Agnew. Chem. Ind. Ed., 34, 1995, 1206–1209.
Knapen et al., Nature, 372, 1994, 659–663.
Hamada et al., Synlett, 1994, 479–481.
Fukuda et al., Synlett, 1995, 825–828.
J. Chem. Soc., Perk. Trans., 1990, 887–895.
Drago et al., J. Am. Chem. Soc., 102, 1980, 1033–1038.
Drago et al., J. Am. Chem. Soc., 102, 1980, 6014–6019.
Watkinson et al., Soc. Chem. Commun., 1994, 2141–2143.
Hauptmann et al., Stereochemie, 1996, 58–67.
Helmchen et al., Methods of Organic Chem., additional supplemental volumen of the 4th Ed., Stereoselective Synthesis, 1995, vol. E21a, Chap. 1, 1–33.
Hopf et al., Liebigs Ann., 1995, 449–451.
Rozenberg et al., Angew. Chem., 106, 1994, 106–108.
Angew. chem. Int. Ed. Engl., 33, 1994, 91–92.
Antonov et al., J. Chem. Soc., Perkin. Trans. I., 1995, 1873–1879.
Matsumoto et al., Bull. Chem. Soc. of Japan, vol. 58, No. 12, 1985, pp. 3621–3622.
Issberner et al., Tetrahedron: Asymmetry, vol. 7, No. 8, Jul. 1995, pp. 2223–2232.

Primary Examiner—Nathan M. Nutter
Attorney, Agent, or Firm—Keil & Weinkauf

[57] ABSTRACT

The present invention relates to dendritic, nitrogen-containing organic compounds containing at least 4 planar-chiral or axial-chiral groups, where these planar-chiral or axial-chiral groups are linked as Schiff's bases to the primary amino groups of compounds of the formula (I)

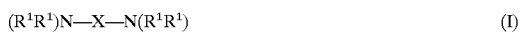

$$(R^1R^1)N\text{—}X\text{—}N(R^1R^1) \quad\quad (I)$$

where $R^1$ is $(R^2R^2)N\text{—}(CH_2)_2\text{—}$ or $(R^2R^2)N\text{—}(CH_2)_3\text{—}$, $R^2$ is hydrogen or $(R^3R^3)N\text{—}CH_2)_2\text{—}$ or $(R^3R^3)N\text{—}(CH_2)_3\text{—}$, $R^3$ is hydrogen or $(R^4R^4)N\text{—}(CH_2)_2\text{—}$ or $(R^4R^4)N\text{—}(CH_2)_3\text{—}$, $R^4$ is hydrogen or $(R^5R^5)\text{—}N\text{—}(CH_2)_2\text{—}$ or $(R^5R^5)N\text{—}(CH_2)_3\text{—}$, $R^5$ is hydrogen or $(R^6R^6)N\text{—}(CH_2)_2\text{—}$ or $(R^6R^6)N\text{—}(CH_2)_3\text{—}$ and $R^6$ is hydrogen, X is an aliphatic and/or aromatic group, which may contain heteroatoms, which are suitable as catalysts for asymmetrical homogeneous catalysis.

11 Claims, 2 Drawing Sheets

DENDRITIC NITROGEN-CONTAINING ORGANIC COMPOUNDS CONTAINING PLANAR-CHIRAL OR AXIAL-CHIRAL END GROUPS AND THE PREPARATION AND USE THEREOF

Dendritic, nitrogen-containing organic compounds containing planar-chiral or axial-chiral end groups, and the preparation and use thereof.

The present invention relates to novel dendritic, nitrogen-containing organic compounds which carry at least 4 planar-chiral or axial-chiral groups on their surface, to their preparation starting from achiral polyamine(imine) dendrimers, and to their use.

Since the publication by E. Buhleier, W. Wehner and F. Vögtle in Synthesis (1978), 137–139 on the general synthesis of structurally perfect and imperfect, highly branched polyamines, work has also been carried out on large-scale methods for the synthesis of dendrimers (cf., for example, WO 93/14147; E. M. M. de Brabander-van den Berg, E. W. Meijer, Angew. Chem. (1993), 105, 1370–1372 or Angew. Chem. Int. Ed. (1993) 31, 1308–1311; C. Wörner, R. Mühlhaupt, Angew. Chem. (1993), 105, 1367–1370; Angew. Chem. Int. Ed. Engl. (1993), 32, 1306–1308; R. Moors, F. V ögtle, Chem. Ber. (1993) 126, 2133–2135). The availability of dendrimers in relatively large amounts is discussed in the publications by J. Issberner, R. Moors and F. Vögtle, Angew. Chem. (1994), 106, 2507–2514, or Angew. Chem. Int. Ed. (1994), 33, 2313–2320; H. B. Mekelburger, W. Jaworek, F. Vögtle, Angew. Chem. (1992) 104, 1609–1614, or Angew. Chem. Int. Ed. (1992) 31, 1571–1576; D. A. Tomalia, H. D. Durst, Top. Curr. Chem. (1993), 165, 193–313. The publications by J. F. G. A. Jansen, H. W. I. Peerlings, E. M. M. de Brabander-van den Berg, E. W. Meijer, Angew. Chem (1995), 107, 1321–1324, or Angew. Chem. Int. Ed. (1995), 34, 1206–1209, describe the synthesis of polyamine dendrimers containing chiral end groups. However, the dendrimers containing only one stereogenic center per functional group have decreasing optical activity with increasing generation number, while dendrimers containing rigid chiral groups have high optical activity which does not drop with increasing generation number.

Dendrimers which carry catalytically active groups on their outer shell should avoid some of the problems of conventional catalysts. In particular, it is hoped that the short reaction time and high activity of homogeneously dissolved catalysts can be combined with the ease of working up reaction mixtures containing heterogeneous catalysts (cf. J. W. J. Knapen, A. W. van der Made, J. C. de Wilde, P. W. M. N. van Leeuwem, P. Wijkens, D. M. Grove, G. van Koten, Nature (1994), Vol. 372, 659–663; Du Bois et al. Inorg. Chem. (1994), 33, 5482; B. B. De B. B. Lohray, S. Sivaram, P. K. Dhal, Tetrah. Asymmetry (1995), 6 (9), 2105–2108 and the references therein; G. Henrici-Olivé, S. Olivé, Angew. Chem. (1974) 86, 1–56). Catalytically active dendrimers generally have good solubility, so that homogeneous reactions are possible, and they can easily be removed from the reaction mixture and recycled (for example by means of osmosis or filtration).

A number of important chiral substances need enantiomerically pure preparation methods, which can be achieved by using chiral auxiliaries (catalysts). Metal salts and metal-salcomine complexes have found a particularly wide variety of uses, for example for asymmetrical Diels-Alder reactions (cf. T. Katsuki et al., Synlett, (1995), 829–830), olefinic β-ketoesters (cf. J. D. White, S. C. Jeffrey, Synlett, (1995), 831 ff.), epoxidation of Z-olefins, for example cycloalkenes, such as stilbene, cyclopentene, cyclohexene, cycloheptene, cyclooctene, dihydronaphthene and indene (cf. S. Chang, J. M. Gavlin, E. N. Jacobsen, J. Am. Chem. Soc. (1994) 116, 6937–6938; P. A. Ganeshpure, S. Satish, Tetrahedr. Lett (1988) 29, 6629–6632), di- and trisubstituted olefins, such as cinnamic esters, maleic acid, maleic esters, imides, amides, anhydrides, monoesters, monoamides, β-substituted acrylic acid, β-substituted acrylic esters and amides, β-substituted styrenes or ring-substituted styrenes and dienes (for example 1,3-cyclooctene and butadiene) (cf. S. Chang, R. M. Heid, E. N. Jacobsen, Tetrahedron Lett. Vol. 35 (1994) 662–672), cis-alkenalkynes (cf. T. Hamada, R. Irie, T. Katsuki, Synlett. (1994), 479–481) and cyclopropanation (cf. T. Fukuda, T. Katsuki, Synlett. (1995), 825–828). Very good and hitherto unachieved enantiomeric excesses of the products were obtained. In certain reactions, although the chirality of the salene complexes is not required, it does not adversely affect the reaction either, for example in the hydrogenation of terminal alkenes and alkynes (cf. J. Chem. Soc., Perk. Trans. (1990), 887 ff.), in the fixing of oxygen (cf. R. S. Drago, J. Gaul, A. Zombeck, D. K. Straub, J. Am. Chem. Soc. (1990) 102, 1033–1038; R. S. Drago, J. P. Cannady, K. A. Leslie, J. Am. Chem. Soc. (1980) 102, 6014–6019) and the splitting of water (cf. M. Watkinson, A. Whiting, C. A. Mc Auliffe, J. Che, Soc. Chem. Commun. (1994), 2141–2143).

It is an object of the present invention to provide novel depdritic, nitrogen-containing organic compounds containing planar-chiral or axial-chiral groups which are readily accessible industrially, do not involve the risk of racemization and act as catalytic centers for further reactions.

We have found that this object is achieved by dendritic, nitrogen-containing organic compounds which contain at least 4 planar-chiral or axial-chiral or helical-chiral groups (axial-chiral and planar-chiral compounds and molecules can, with respect to their molecular chirality, be specified not only as axial S and R (aS, aR) or planar-chiral S and planar-chiral R (pS, pR), but advantageously frequently also, as in the book by Hauptmann/Mann (S. Hauptmann, G. Mann, Stereochemie, Spektrum Akademischer Verlag, Heidelberg, 1996, 58–67) and in the paper by G. Helmchen (G. Helmchen in Houben-Weyl, Methods of Organic Chemistry, Additional and Supp. Vol. of the 4th Edition, Stereoselective Synthesis (Editors: G. Helmchen, R. W. Hoffmann, J. Mulzer, E. Schaumann, Georg Thieme Verlag, Stuttgart, 1995, Vol. E 21a, Chapter 1, pp. 1–33) can be regarded as helical-chiral species, ie. can be characterized and specified as (−) and (+) P and M with respect to their direction of chirality), where these planar-chiral or axial-chiral groups are linked as Schiff's bases to the primary amino groups of compounds of the formula (I)

$$(R^1R^1)N-X-N(R^1R^1) \qquad (I)$$

where $R^1$ is $(R^2R^2)N-(CH_2)_2-$ or $(R^2R^2)N-(CH_2)_3-$,
$R^2$ is hydrogen or $(R^3R^3)N-(CH_2)_2-$ or $(R^3R^3)N-(CH_2)_3-$,
$R^3$ is hydrogen or $(R^4R^4)N-(CH_2)_2-$ or $(R^4R^4)N-(CH_2)_3-$,
$R^4$ is hydrogen or $(R^5R^5)-N-(CH_2)_2-$ or $(R^5R^5)N-(CH_2)_3-$,
$R^5$ is hydrogen or $(R^6R^6)N-(CH_2)_2-$ or $(R^6R^6)N-(CH_2)_3-$
and
$R^6$ is hydrogen
X is 

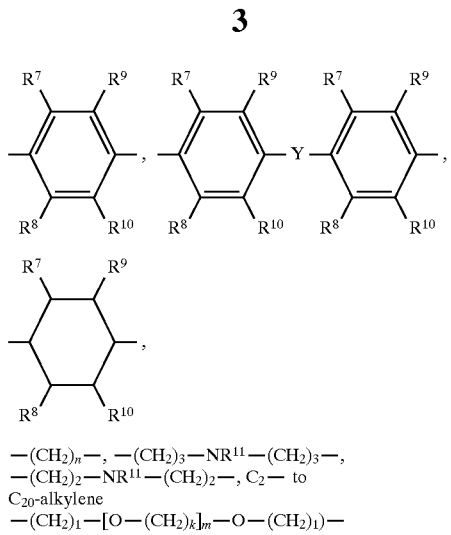

$-(CH_2)_n-$, $-(CH_2)_3-NR^{11}-(CH_2)_3-$,
$-(CH_2)_2-NR^{11}-(CH_2)_2-$, $C_2-$ to $C_{20}$-alkylene
$-(CH_2)_l-[O-(CH_2)_k]_m-O-(CH_2)_l-$ where Y is $CR^7R^9$, oxygen, C=O or $SO_2$, n is from 2 to 20, l and k are from 2 to 6, and m is from 1 to 40, $R^7$ $R^8$, $R^9$ and $R^{10}$ are hydrogen or $C_1$- to $C_6$-alkyl, $R^{11}$ is $C_1$- to $C_{20}$-alkyl, $C_2$- to $C_{20}$-dialkylamino-$C_2$- to $C_{10}$-alkyl, $C_1$- to $C_{10}$-alkoxy-$C_2$- to $C_{10}$-alkyl, $C_2$- to $C_{20}$-hydroxyalkyl, $C_3$- to $C_{12}$-cycloalkyl, $C_4$- to $C_{20}$-cycloalkylalkyl, $C_2$- to $C_{20}$-alkenyl, $C_4$- to $C_{30}$-dialkylaminoalkenyl, $C_3$- to $C_{30}$-alkoxyalkenyl, $C_3$- to $C_{20}$-hydroxyalkenyl, $C_5$- to $C_{20}$-cycloalkylalkenyl, aryl or $C_7$- to $C_{20}$-aralkyl which is unsubstituted or monosubstituted to pentasubstituted by $C_1$- to $C_8$-alkyl, $C_2$- to $C_8$-dialkylamino, $C_1$- to $C_8$-alkoxy, hydroxyl, $C_3$- to $C_8$-cycloalkyl or $C_4$- to $C_{12}$-cycloalkylalkyl, or together are an alkylene chain which may be interrupted by nitrogen or oxygen, such as ethylene oxide, propylene oxide, butylene oxide or $-CH_2-CH(CH_3)-O-$ or polyisobutylene having 1 to 100 isobutylene units.

Dendritic compounds containing planar-chiral groups which are preferred in accordance with the invention are those in which the planar-chiral groups linked to dendritic nitrogen-containing organic compounds of the formula (I) are those of the formula

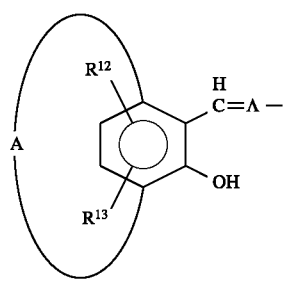

where =N— is in each case the nitrogen of the Schiff's base obtained from the primary amino group, $R^{12}$ and $R^{13}$, independently of one another, can have the following nmeanings:

H, alkyl having 1 to 22 carbon atoms,
O—$C_1$- to $C_{22}$-alkyl,
S—$C_1$- to $C_{22}$-alkyl,

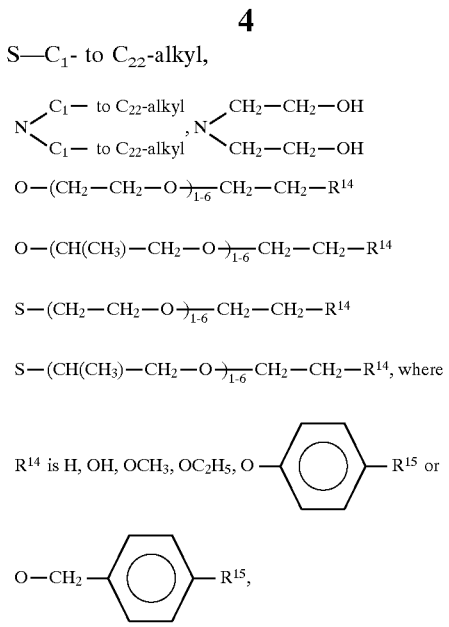

$O-(CH_2-CH_2-O)_{1-6}CH_2-CH_2-R^{14}$ $O-(CH(CH_3)-CH_2-O)_{1-6}CH_2-CH_2-R^{14}$ $S-(CH_2-CH_2-O)_{1-6}CH_2-CH_2-R^{14}$ $S-(CH(CH_3)-CH_2-O)_{1-6}CH_2-CH_2-R^{14}$, where $R^{14}$ is H, OH, $OCH_3$, $OC_2H_5$, O—⟨⟩—$R^{15}$ or

O—$CH_2$—⟨⟩—$R^{15}$, and $R^{15}$ is H, alkyl having 1 to 4 carbon atoms, O—$C_1$- to $C_4$-alkyl, halogen, CN or $NO_2$,

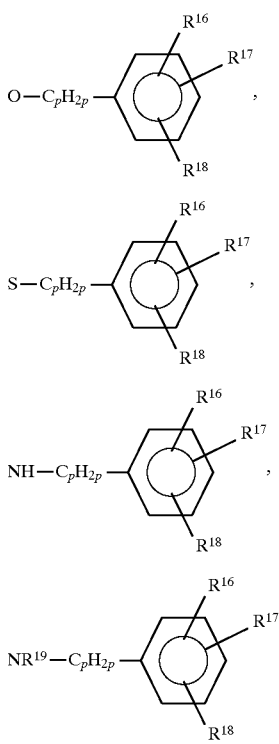

in which p can be 0 or from 1 to 22, and $R^{16}$, $R^{17}$ and $R^{18}$, independently of one another, are H, alkyl having 1 to 22 carbon atoms, O—$C_1$- to $C_{22}$-alkyl, S—$C_1$- to $C_{22}$-alkyl;

N($C_1$- to $C_{22}$-alkyl)($C_1$- to $C_{22}$-alkyl);

-continued

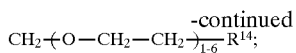

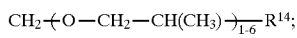

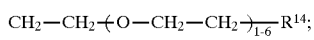

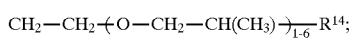

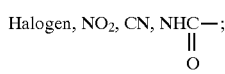

$R^{19}$ is alkyl having 1 to 20 carbon atoms,

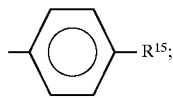

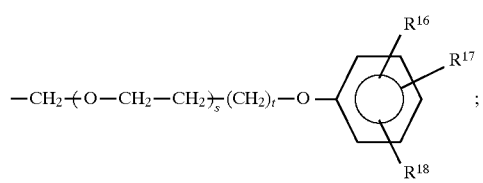

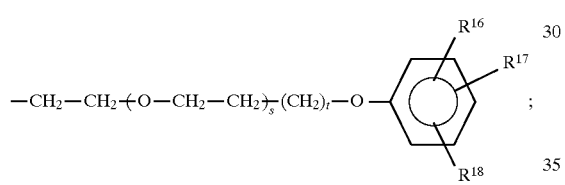

where s=0, 1 or 2
and t=0 or 1, a five- or six-membered nitrogen-, oxygen- or sulfur-containing heteroaromatic radical, which is unsubstituted or substituted by alkyl having 1 to 22 carbon atoms, O—$C_1$- to $C_{22}$-alkyl, S—$C_1$- to $C_{22}$-alkyl, NH—$C_1$- to $C_{22}$-alkyl

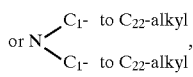

—C≡CH, —$CH_2$—C≡CH, —$CH_2$—C≡C—$CH_3$, —$CH_2$—C≡C—$C_2H_5$, —$CH_2$—$CH_2$—C≡CH,

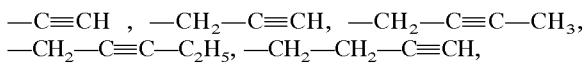

and A is —$(CH_2)$—$_{4 \ to \ 8}$, —$CH_2$—O—$CH_2$—$CH_2$—$OCH_2$—, —$CH_2$—O—$CH_2$—$CH(CH_3)$—O—$CH_2$—, —$CH_2$—O—$CH_2$—$CH_2$—$CH_2$—O—$CH_2$—, —$CH_2$—O—$(CH_2)_4$—O—$CH_2$—, —O—$(CH_2$—$CH_2$—O$)_{1 \ or \ 2}$, —O—$(CH_2$—$CH(CH_3)$—O$)_{1 \ or \ 2}$ or

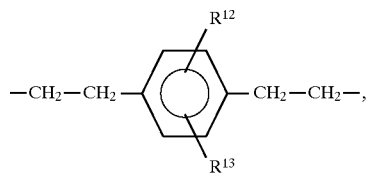

where $R^{12}$ and $R^{13}$, independently of one another, are as defined above or are halogen, CN, $NO_2$, —N=N—$R^{20}$ or

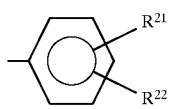

where
$R^{20}$ is phenyl which is unsubstituted or substituted by $NO_2$, CN, halogen, $C_1$- to $C_4$-alkyl, $C_1$- to $C_4$-alkoxy, $C_1$- to $C_4$-alkylthio or $C_1$- to $C_4$-alkylamino,
$R^{21}$ and $R^{22}$, independently of one another, are $C_1$- to $C_4$-alkyl, $C_1$- to $C_4$-alkoxy, CN, $NO_2$ or halogen,

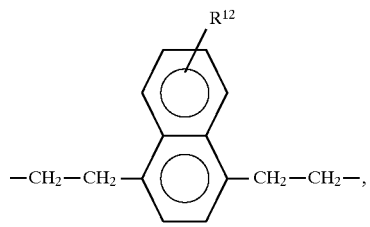

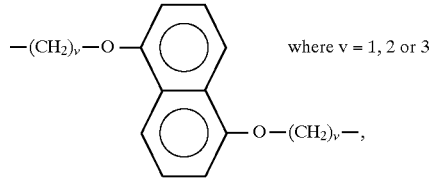

where v = 1, 2 or 3

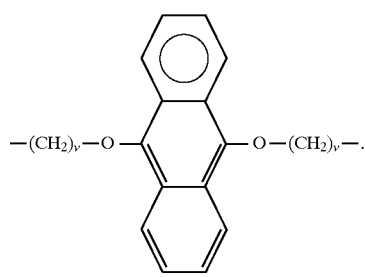

Preferred dendritic compounds containing axial-chiral groups are those in which the axial-chiral groups linked to dendritic nitrogen-containing organic compounds of the formula (I) are those of the formula

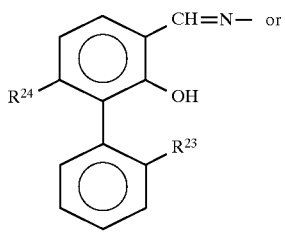

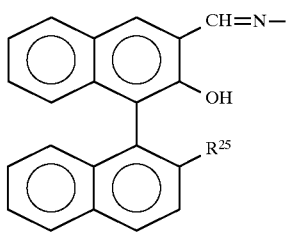

where
=N— is in each case the nitrogen of the Schiff's base obtained from the primary amino group,
$R^{23}$ and $R^{24}$, independently of one another, are $C_1$- to $C_{22}$-alkyl, $C_1$- to $C_6$-alkyloxy or phenyl which is unsubstituted or substituted by halogen, CN, $NO_2$, $C_1$- to $C_4$-alkyl or $C_1$- to $C_4$-alkoxy, or

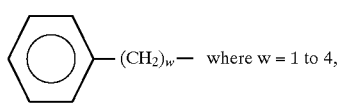 where w = 1 to 4, with the proviso that at least one of $R^{23}$ and $R^{24}$ is tert-butyl or a radical which prevents the free 360° rotatability of the phenyl radicals, and $R^{25}$ is tert-butyl or phenyl which is unsubstituted or substituted by halogen, CN, $NO_2$, $C_1$- to $C_4$-alkyl or $C_1$- to $C_4$-alkoxy.

The present invention furthermore provides the novel dendritic compounds containing planar-chiral or axial-chiral groups in the form of metal complexes of transition metals, such as Ag(I), Mn(II), Mn(III), Mn(IV), Co(II), Co(III), Ni(II), Cu(II) and Pd(II) salts.

These metal complexes can be prepared by dissolving or dispersing the novel dendritic compounds containing planar-chiral or axial-chiral groups in a suitable solvent together with transition-metal salts at from room temperature to the boiling point of the solvent, subsequently removing the solvent, and washing the resultant complexes with water in order to remove excess metal salt.

However, the transition metal complexes can also be obtained simultaneously during preparation of the Schiff's bases by adding is the transition-metal salts to the reaction mixture.

The present invention also provides a process for the preparation of novel dendritic, nitrogen-containing organic compounds containing at least 4 planar-chiral groups by reacting compounds of the formula (I) with hydroxyaldehydes of the formula

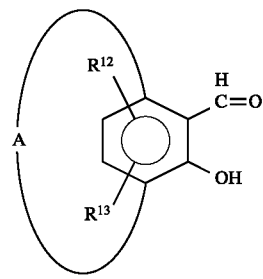

in the presence of water-binding substances or substances which rentrain water on distillation.

The present invention furthermore provides a process for the preparation of novel dendritic, nitrogen-containing organic compounds containing at least 4 axial-chiral groups by reacting compounds of the formula (I) with hydroxyaldehydes of the formula

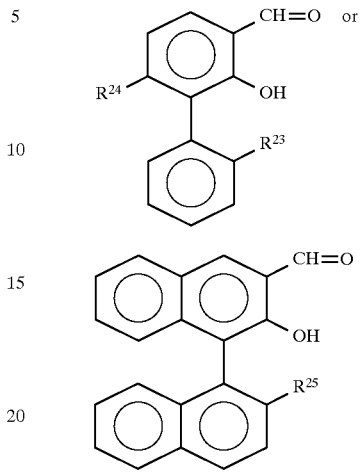

in the presence of water-binding substances or substances which entrain water on distillation.

The present invention also provides the use of novel dendritic, nitrogen-containing organic compounds containing planar-chiral or axial-chiral groups and transition-metal complexes thereof as catalysts for asymmetrical homogeneous catalysis.

The following details also apply to the novel compounds and preparation processes.

If $R^1$ to $R^{25}$ are or contain alkyl and contain more than 3 carbon atoms, these can be straight-chain or branched and can also contain cyclic, for example three-, five- or six-membered radicals.

Amino compounds of the formula (I) and their preparation are disclosed in DE-A 44 40 551.

The amino compounds of the formula (I) are reacted in accordance with the invention with hydroxyaldehydes of the formula

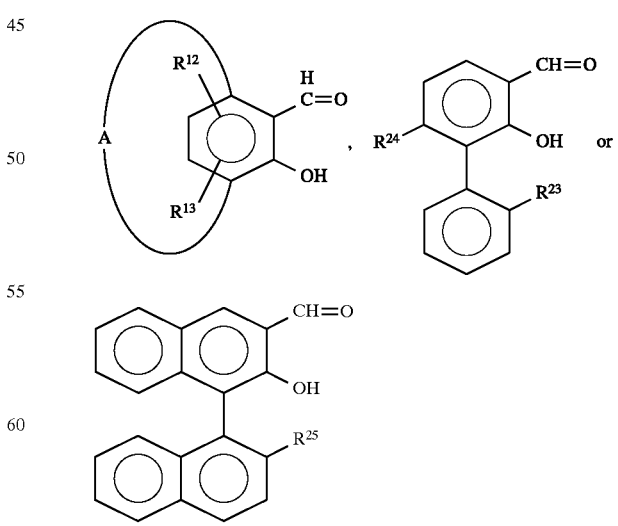

to give dendritic Schiff's bases containing planar-chiral or axial-chiral groups.

An example of a planar-chiral group of the formula

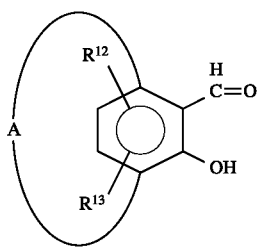

is 5-formyl-4-hydroxy[2.2]paracyclophane (=FHPCP) (1).

FHPCP (cf. H. Hopf, D. G. Barrett, Liebigs Ann. 1995, 449–451) can be synthesized as described by Belokon et al. (cf. V. Rozenberg, V. Khartinov, D. Antonov, E. Sergeeva, A. Aleshkin, N. Ikonnikov, S. Orlova, Y. Belokon, Angew. Chem. (1994) 106, 106–108; Angew. Chem. Int. Ed. Engl. (1994) 33, 91; D. Y. Antonov, Y. N. Belokon, N. S. Ikonnikov, S. A. Orlova, A. P. Pisarevski, N. I. Raevski, V. I. Rozenburg, E. V. Sergeeva, Y. T. Struchkov, V. I. Tararov, E. V. Vorotsov, J. Chem. Soc., Perkin Trans. I., (1995) 1873–1879) and by Hopf and Barrett and separated into the enantiomers via Schiff's base/Cu complexes and by HPLC. The resultant enantiomerically pure aldehyde can be used for all further syntheses.

The condensation of the enriched and enantiomerically pure aldehyde FHPCP (1) with the dendritic polyamine of the formula (2a), (2b) or (2c) (first to third generation, reacted with four (gives compound (3a)), eight (gives compound (3b)) or sixteen (gives compound (3c)) $NH_2$ groups) can be carried out at room temperature in a suitable organic solvent (for example dichloromethane) using a dehydrating agent, for example sodium sulfate, magnesium sulfate, molecular sieve, calcium chloride, NaOH, KOH, LiOH or MgO or by boiling under atmospheric pressure at the reflux temperature in benzene, toluene or xylene, for example using a Dean-Stark trap. The tetra-, octa- or hexadecaimine (compounds (3a) to (3c)) respectively is obtained. Naturally, all other known and conventional condensation methods for the preparation of Schiff's bases are also suitable so long as no other reaction (for example with the OH group in the ortho-position of FHPCP) occurs.

After the condensation reaction, the resultant product is washed a number of times with hot methanol in order to remove excess FHPCP. The dendritic imine, whose purity can be determined by $^1$H-NMR spectroscopy, is left as an orange-yellow solid.

The novel transition-metal complexes of the dendritic, nitrogen-containing organic compounds containing planar-chiral groups can be prepared by dissolving or dispersing the dendritic compounds containing chiral groups together with transition-metal salts, for example Ag(I), Mn(II), Mn(III), Mn(IV), Co(II), Co(III), Ni(II), Pd(II) or Cu(II) salts, for example acetates, triflates, tosylates, mesylates, nitrates and—apart from Ag(I)—halides and pseudohalides (for example $SCN^\ominus$) of these transition metals in appropriate organic solvents, for example methanol, ethanol, propanol, butanol, ethylene glycol, the methyl, ethyl, propyl and higher ethers thereof, dichloromethane, chloroform, benzene, toluene, xylene, dimethylformamide, N-methylpyrrolidone, dimethyl sulfoxide, tetrahydrofuran or tetrahydropyran, under a nitrogen atmosphere at from room temperature to the boiling point of the organic solvent, subsequently removing the solvent, and washing the transition-metal complexes with water by shaking in order to remove excess metal salt. In the case of the preparation of Mn(III) complexes, the dendritic compounds containing chiral groups can be dissolved in an organic solvent together with Mn(II) salts, and oxygen or air blown through the solution during the complexation.

Alternatively, the transition-metal ion complexes can also be prepared simultaneously during preparation of the Schiff's bases by adding the abovementioned transition-metal salts to the reaction mixture.

A comparison of the circular dichroism (=CD) spectrum (FIG. 1) of an individual chiral salene unit (4) (formula on page 17) with that of chiral multi-salene dendrimers (3a)–(3c) shows no difference, which indicates that most or all salene units on the dendrimer surface have not undergone complexation by metal salts.

A comparison of the circular dichroism (=CD) spectra of dendrimers containing chiral groups with and without anhydrous cobalt(II) chloride complexing agent shows a clear difference. For example, the CD spectra of the chiral dendrimers (3a)–(3c) with and without cobalt(II) chloride complexing the salene units shows a clear difference, which indicates that most or all salene units are complexed and consequently for the complex is a dendrimer containing a large number of catalytic centers.

Scheme 1 shows the reactions of the 1st to 3rd generation of polyamine dendrimers of the formula (2a), (2b) and (2c) containing 4, 8 and 16 $NH_2$ groups respectively with FHPCP, and structure (4) (page 17).

Figure 1:
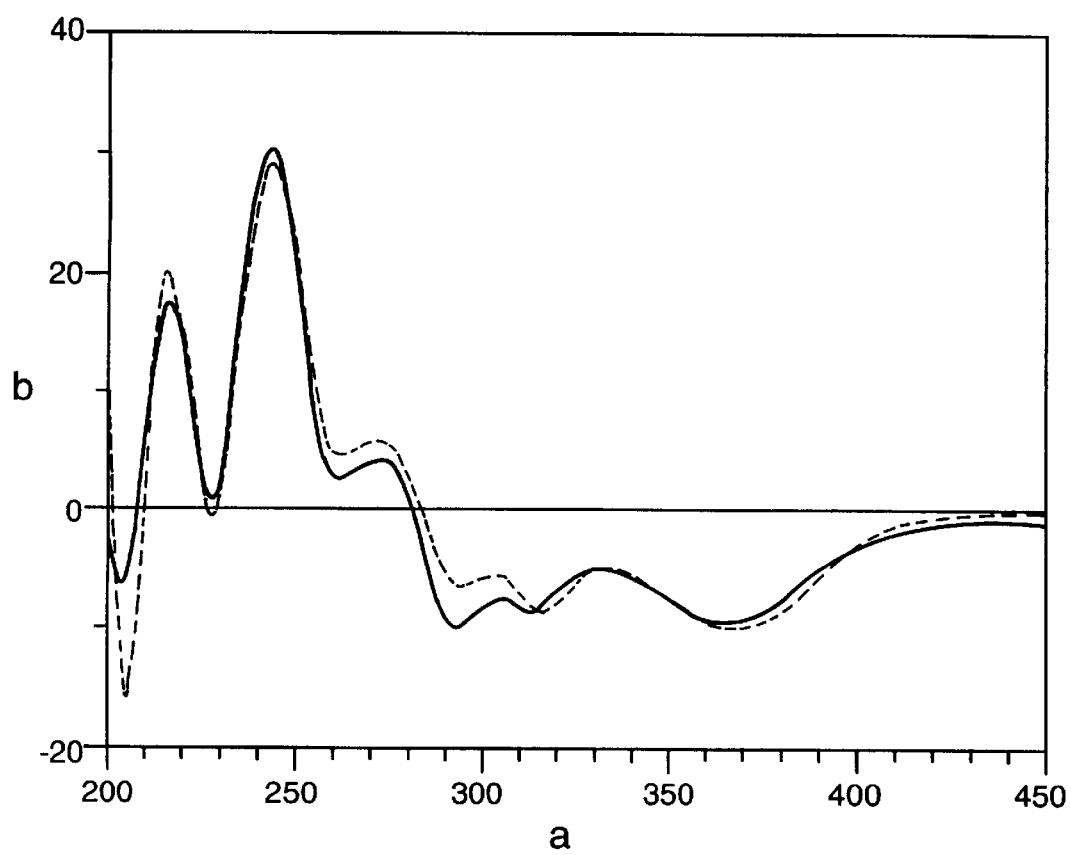
FIG. 1 shows the CD spectra of (4) (. . .) and (3c) (—) dissolved in dichloromethane; a=wavelength [nm]; b=Δε.
Figure 2:
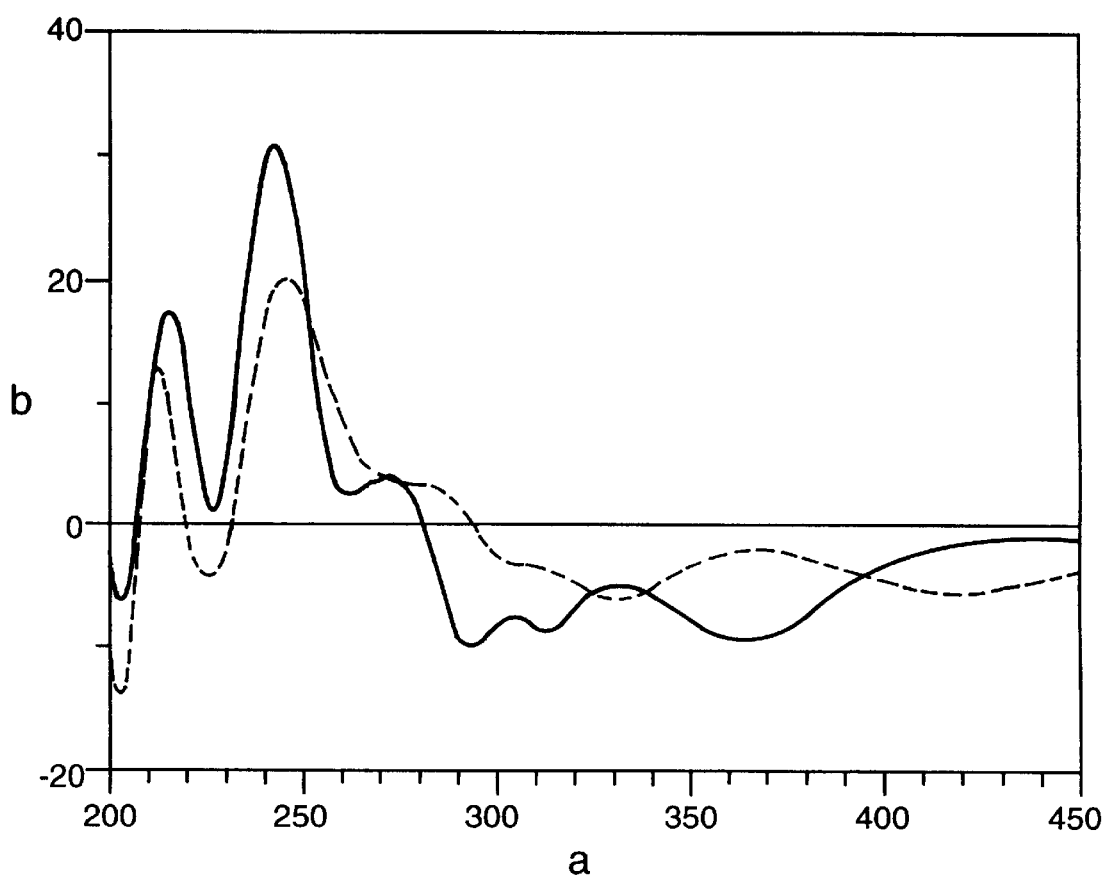
FIG. 2 shows the CD spectra of (3c) dissolved in dichloromethane in the absence of a transition-metal salt (—) and after addition of anhydrous cobalt(II) chloride (. . .); a=wavelength [nm]; b=Δε.

Scheme 1:
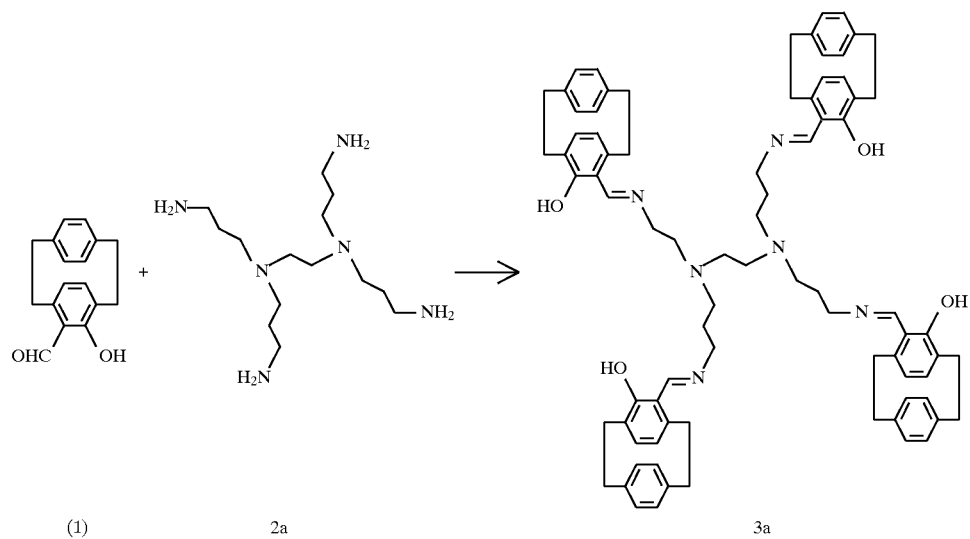
(1)  2a  3a
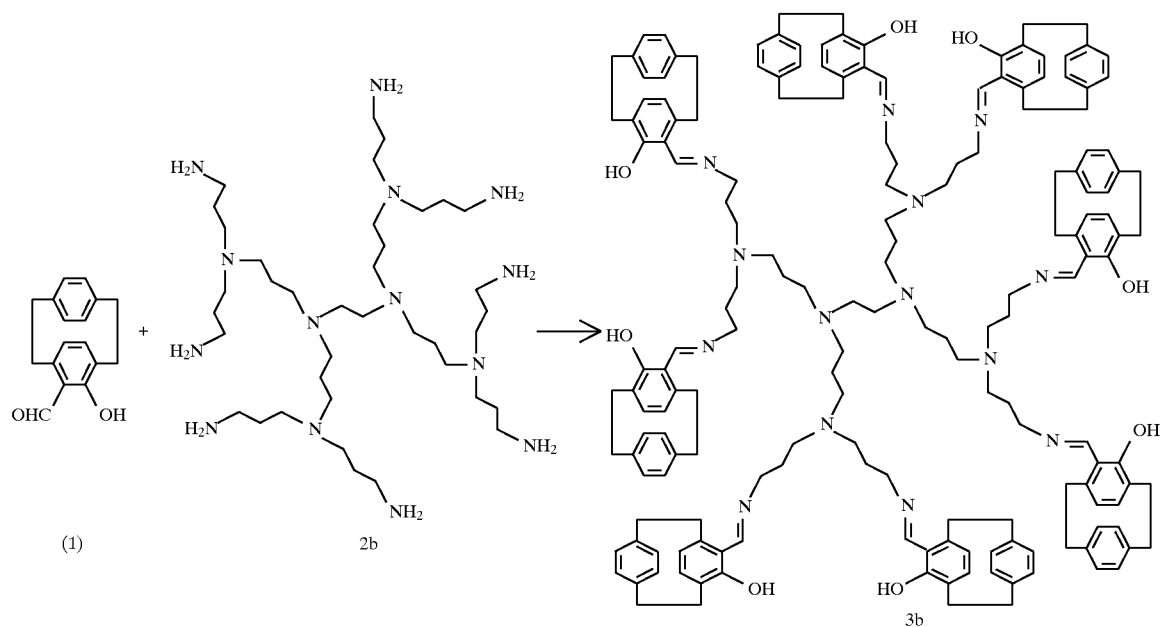
(1)  2b  3b

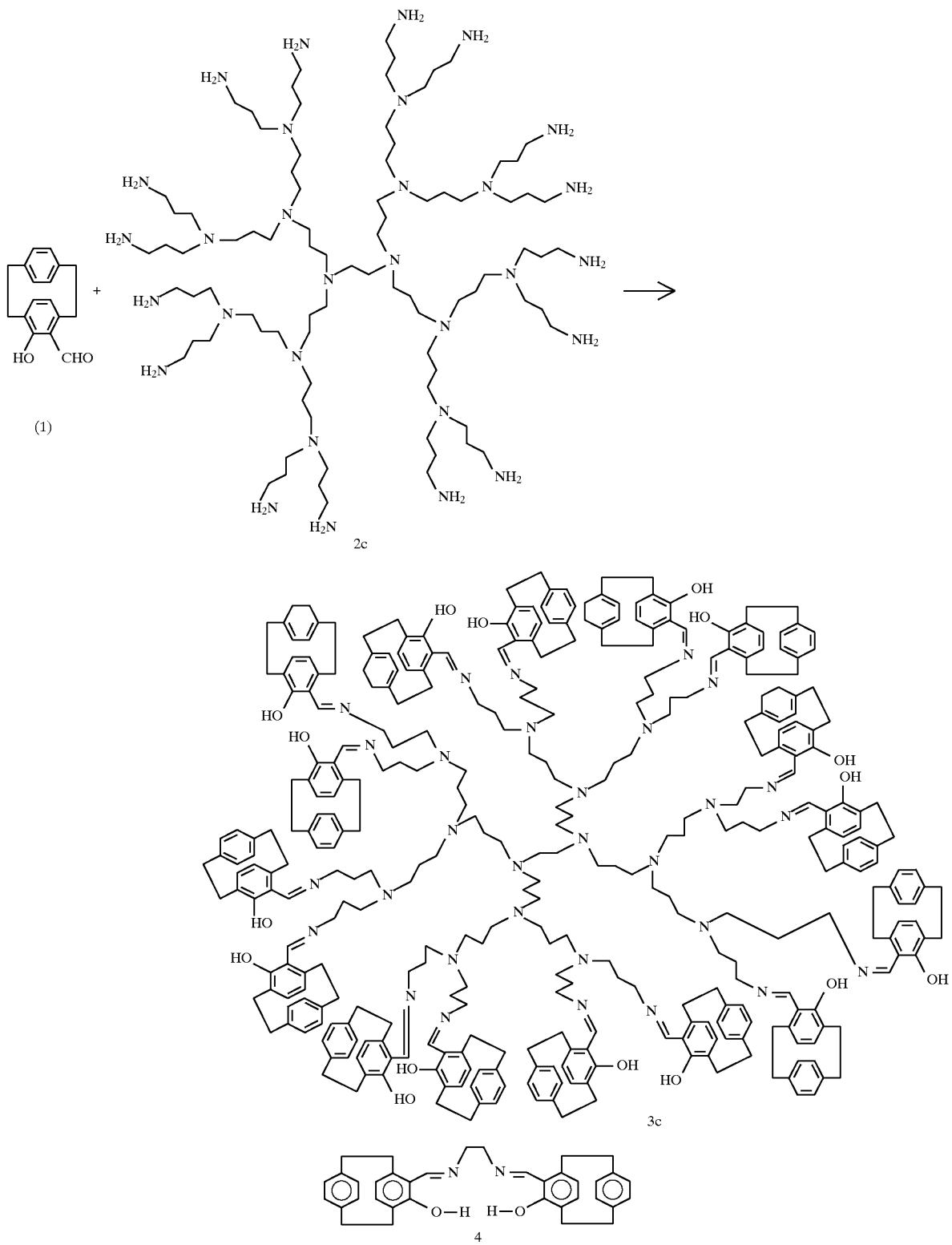
EXAMPLES
General procedure for the synthesis of the Schiff's bases 3a, b, c, 4
(3b) 7.5 mg (0.03 mmol) of $(^+)_D$-(R)-5-formyl-4-hydroxy [2.2]-paracyclophane (1) are dissolved in 25 ml of solvent. 2.7 mg (0.004 mmol) of the octaamine (2b) dissolved in 10 ml of solvent are slowly added dropwise at 60° C. The solution is then heated at the boil for 8 hours on a heavy-phase separator. The solvent is removed under reduced pressure, and the resultant orange-yellow oil is washed repeatedly with hot methanol. Removal of all volatile constituents in a high vacuum leaves an orange-yellow solid.

The purity of the Schiff's bases was determined by $^1$H-NMR spectroscopy and was 95%. Yield: 7.0 mg (69%), orange-yellow, m.p. 42°, $[\alpha]_D^{25°}$=+478 (c=0.2 in CH$_2$Cl$_2$); $^1$H-NMR (400 Hz, CDCl$_3$, 25° C.) : δ1.5–1.6 (m, 16H, CH$_2$), 1.7–1.8 (m, 16H, CH$_2$), 2.42–2.57 (m, 36H, CH$_2$), 2.59–2.80 (m, 16H, CH$_2$), 2.88–2.97 (m, 8H, CH$_2$), 2.99–3.14 (m, 16H, CH$_2$), 3.24–3.32 (m, 8H, CH$_2$), 3.33–3.42 (m, 8H, CH$_2$), 3.46–3.57 (m, 16H, CH$_2$), 6.06 (d, $^3$J(H,H)=7.6 Hz, 8H, CH), 6.12 (dd, $^3$J(H,H)=7.6 Hz, $^4$J(H,H)=1.7 Hz, 8H, CH), 6.34 (dd, $^3$J(H,H)=7.6 Hz, $^4$J(H,H)=1.7 Hz, 8H, CH), 6.39 (d, $^3$J(H,H)=7.6 Hz, 8H, CH), 6.50 (dd, $^3$J(H,H)=7.6 Hz, $^4$J(H,H)=1.7 Hz, 8H, CH), 6.77 6.(dd, $^3$J(H,H)=7.6 Hz, $^4$J(H,H)=1.7 Hz, 8H, CH), 8.06 (s, 8H, CHN), 14.2 (br.s, OH); $^{13}$C-NMR (100 Hz, CDCl$_3$, 25° C.): δ=24.7 (C$_s$), 28.9 (C$_s$), 32.2 (C$_2$), 33.9 (C$_s$), 35.3 (C$_s$), 51.7 (C$_s$), 52.2 (C$_s$), 56.9 (C$_s$), 119.1 (C$_q$), 123.7 (C$_t$), 126.6 (C$_t$), 128.1, 130.5 (C$_t$), 132.0 (C$_t$), 133.4 (C$_t$), 137.4 (C$_t$), 137.5 C$_q$), 140.1 (C$_q$), 140.1 (C$_q$), 142.0 (C$_q$), 162.2 (CH=N), 163.0 (C$_q$); MS (positive-FABm NBA) m/z=2620.7 (M$^+$ [C$_{174}$H$_{204}$N$_{14}$O$_8$]+H, 20%, C$_{174}$H$_{204}$N$_{14}$O$_8$ (2619.6); CHN analysis (calc.:) H: 7.85%, C: 79.87%, N: 7.49%, O 4.89%.

(3a) $^1$H-NMR (400 Hz, CDCl$_3$, 25° C.) : δ=1.81 (t, $^3$J(H,H)=6.2 Hz; 8H, CH$_2$), 2.45–2.76 (m, 24H, CH$_2$), 2.93 (td, 4H, CH$_2$), 3.0–3.1 (m, 8H, CH$_2$), 3.25–3.40 (m, 8H, CH$_2$), 3.45–3.60 (m, 8H, CH$_2$), 6.07 (dd, $^3$J(H,H)=7.6 Hz, $^4$J(H,H)=1 Hz, 4H, CH), 6.13 (d, $^3$J(H,H)=7.9 Hz, 4H, CH), 6.34 (dd,$^3$J(H,H)=7.9 Hz, $^4$J(H,H) =1.7 Hz, 4H, CH), 6.40 (d, $^3$J(H,H)=7.6 Hz, 4H, CJ), 6.50(d, $^3$J(H,H)=7.9 Hz, 4H, CH), 6.78 6.(dd, $^3$J(H,H)=7.7 Hz, $^4$J(H,H)=1.7 Hz, 4H, CH), 8.06 (s, 4H, CHN), 14.2 (br.s, OH); $^{13}$C—NMR (100 Hz, CDCl$_3$, 25° C.) : δ24.7 (C$_s$), 28.9 (C$_s$), 29.9 (C$_s$), 32.2 (C$_s$), 33.9 (C$_s$), 35.3 (C$_s$), 51.7 (C$_s$), 52.2 (C$_s$), 56.9 (C$_s$), 119.1 (C$_q$), 123.7 (C$_t$), 126.6$_t$), 128.1; 130.5 (C$_t$), 1320 (C$_t$), 133.4 (C$_t$), 137.4 (C$_t$), 137.5 (C$_q$), 140.1 (C$_q$), 142.0 (C$_q$), 162.2 (CH=N), 163.0 (C$_q$),; MS (positive-FAB, m-NBA) m/z= 1225.8 (M$^+$[C$_{82}$H$_{92}$N$_6$O$_4$]—H, 100%), C$_{82}$H$_{92}$N$_6$O$_4$ (1224.72). CHN analysis (calc.:) H: 7.57%, C: 80.36%, N: 6.86%, O 5.22%.

(3c) $^1$H-NMR (400 Hz, CDCl$_3$, 25° C.) : δ=1.5–1.85 (br.s, 64H, CH$_2$), 2.3–2.7 (m, 124H, CH$_2$), 2.85–2.95 (m, 16H, CH$_2$), 3.0–3.15 (m, 32H, CH$_2$), 3.2–3.4 (m, 32H, CH$_2$), 3.45–3.6 (m, 32H, CH$_2$); 6.06 (d, $^3$J(H,H)=7.6 Hz, 16H, CH), 6.12 (d, $^3$J(H,H)=7.6 Hz, 16H, CH), 6.34 (d, $^3$J(H,H) =7.6 Hz, 16H, CH), 6.39 (d, $^3$J(H,H)=7.6 Hz, 16H, CH), 6.50 (d, $^3$J(H,H)=7.6 Hz, 16H, CH), 6.77 (d, $^3$J(H,H)=7.6 Hz, 16H, CH), 8.06 (s, 16H, CHN), 14.2 (br.s, OH); $^{13}$C—NMR (100 Hz, CDCl$_3$, 25° C.) : δ=29.4 (C$_s$), 28.5 (C$_s$), 29.9 (C$_s$), 32.2 (C$_s$), 33.9 (C$_s$), 35.3 (C$_s$), 51.4 (C$_s$), 56.6 (C$_s$), 119.1 (C$_q$), 123.7 (C$_t$), 126.6 (C$_t$), 128.1, 130.5 (C$_t$), 132.0 (C$_t$), 133.4 (C$_t$), 147.4 (C$_t$), 137.5 (C$_q$), 140.1 (C$_q$), 142.0 (C$_q$), 162.5 (CH=N), 163.0 (C$_q$); C$_{358}$H$_{428}$N$_{30}$O$_{16}$ (5407.53); CHN analysis C$_{358}$H$_{428}$N$_{30}$O$_{16}$. 4 HCCl$_3$ calc. (found) %: H: 7.40 (7.71), C: 73.88 (73.77), N: 7.14 (7.06). Resolution of the enantiomers by HPLC; column: cellulose tris(3,5-dimethylphenylcarbamate (CDMPC), 500×4.6 mm. Eluent: n-Hexane/isopropanol 9:1, 0.3 ml min$^{-1}$. Pressure: 3 bar; temperature 25° C. Detection: UX, λ=254 nm; t$_r$ [(+)D$^{-1}$]=26 min; t$_r$ [(−)D$^{-1}$]=35 min; k' [(−)D$^{-1}$]=4.54; k' [(+)D$^{-1}$]=5.92; α=1.30; R=1.89.

$[\alpha]_{578}^{20}$[(R)-1]=+588(c=0.02;CH$_2$Cl$_2$) Perkin-Elmer 241 polarimeter.

CD measurements using a JASCO J 720 spectropolarimeter, 0.001 g/ml solution in dichloromethane; 0.02 mm cell.

We claim:
1. A dendritic nitrogen-containing organic compound which contains at least 4 planar-chiral or axial-chiral groups, where these planar-chiral or axial-chiral groups are linked as Schiff's bases to the primary amino groups of compounds of the formula (I)

where
R$^1$ is (R$^2$R$^2$)N—(CH$_2$)$_2$— or (R$^2$R$^2$)N—(CH$_2$)$_3$—,
R$^2$ is hydrogen or (R$^3$R$^3$)N—(CH$_2$)$_2$— or (R$^3$R$^3$)N—(CH$_2$)$_3$—,
R$^3$ is hydrogen or (R$^4$R$^4$)N—(CH$_2$)$_2$— or (R$^4$R$^4$)N-(CH$_2$)$_3$—,
R$^4$ is hydrogen or (R$^5$R$^5$)—N—(CH$_2$)$_2$— or (R$^5$R$^5$)N—(CH$_2$)$_3$—,
R$^5$ is hydrogen or (R$^6$R$^6$)N—(CH$_2$)$_2$— or (R$^6$R$^6$)N—(CH$_2$)$_3$—and
R$^6$ is hydrogen
x is

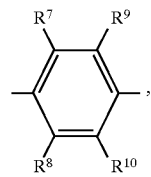

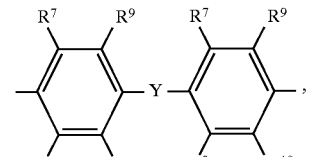

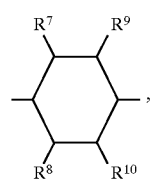

—(CH$_2$)$_n$—, —(CH$_2$)$_3$—NR$^{11}$—(CH$_2$)$_3$—, —(CH$_2$)$_2$—NR$^{11}$—(CH$_2$)$_2$—, C$_2$— to C$_{20}$-alkylene —(CH$_2$)$_1$—[O—(CH$_2$)$_k$]$_m$—O—(CH$_2$)$_1$)—
where Y is CR$^7$R$^9$, oxygen, C=O or SO$_2$, n is from 2 to 20, 1 and k are from 2 to 6, and m is from 1 to 40,
R$^7$, R$^8$, R$^9$ and R$^{10}$ are hydrogen or C$_1$- to C$_6$-alkyl,
R$^{11}$ is C$_1$- to C$_{20}$-alkyl, C$_2$- to C$_{20}$-dialkylamino-C$_2$- to C$_{10}$-alkyl, C$_1$- to C$_{10}$-alkoxy-C$_2$- to C$_{10}$-alkyl, C$_2$- to C$_{20}$-hydroxyalkyl, C$_3$- to C$_{12}$-cycloalkyl, C$_4$- to C$_{20}$-cycloalkylalkyl, C$_2$- to C$_{20}$-alkenyl, C$_4$- to C$_{30}$-dialkylaminoalkenyl, C$_3$- to C$_{30}$-alkoxyalkenyl, C$_3$- to C$_{20}$-hydroxyalkenyl, C$_5$- to C$_{20}$-cycloalkylalkenyl, aryl or C$_7$- to C$_{20}$-aralkyl which is unsubstituted or monosubstituted to pentasubstituted by C$_1$- to C$_8$-alkyl, C$_2$- to C$_8$-dialkylamino, C$_1$- to C$_8$-alkoxy, hydroxyl, C$_3$- to C$_8$-cycloalkyl or C$_4$- to C$_{12}$-cycloalkylalkyl, or together are an alkylene chain which may be interrupted by nitrogen or oxygen, such as ethylene oxide, propylene oxide, butylene oxide or —CH$_2$—CH(CH$_3$)—O— or polyisobutylene having 1 to 100 isobutylene units.

2. A compound as claimed in claim 1, wherein the planar-chiral groups linked to dendritic nitrogen-containing organic compounds of the formula (I) are those of the formula

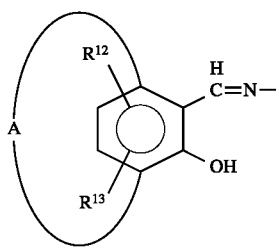

where =N— is in each case the nitrogen of the Schiff's base obtained from the primary amino group, $R^{12}$ and $R^{13}$, independently of one another, can have the following meanings:
H, alkyl having 1 to 22 carbon atoms,
O—$C_1$- to $C_{22}$-alkyl,
S—$C_1$- to $C_{22}$-alkyl,

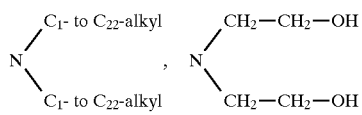

O—(CH$_2$—CH$_2$—O$\rightarrow$)$_{1-6}$CH$_2$—CH$_2$—R$^{14}$
O—(CH(CH$_3$)—CH$_2$—O$\rightarrow$)$_{1-6}$CH$_2$—CH$_2$—R$^{14}$
S—(CH$_2$—CH$_2$—O$\rightarrow$)$_{1-6}$CH$_2$—CH$_2$—R$^{14}$
S—(CH(CH$_3$)—CH$_2$—O$\rightarrow$)$_{1-6}$CH$_2$—CH$_2$—R$^{14}$,
where
$R^{14}$ is H, OH, OCH$_3$, OC$_2$H$_5$

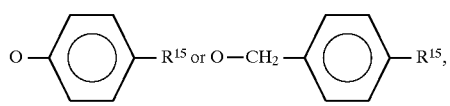

and $R^{15}$ is H, alkyl having 1 to 4 carbon atoms, O—$C_1$- to $C_4$-alkyl, halogen, CN or NO$_2$,

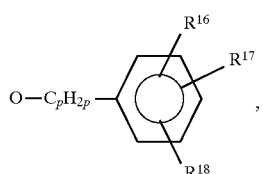

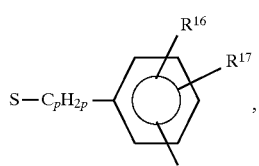

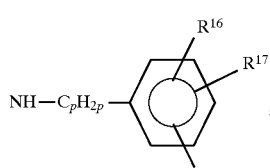

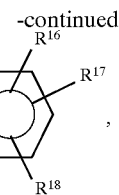

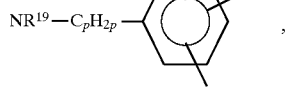

in which p can be 0 or from 1 to 22, and $R^{16}$, $R^{17}$ and $R^{18}$, independently of one another, are H, alkyl having 1 to 22 carbon atoms, O—$C_1$- to $C_{22}$-alkyl,
S—$C_1$- to $C_{22}$-alkyl,

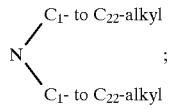

CH$_2$—(O—CH$_2$—CH$_2$—)$_{1-6}$R$^{14}$;
CH$_2$—(O—CH$_2$—CH(CH$_3$)—)$_{1-6}$R$^{14}$;
CH$_2$—CH$_2$—(O—CH$_2$—CH$_2$—)$_{1-6}$R$^{14}$;
CH$_2$—CH$_2$—(O—CH$_2$—CH(CH$_3$)—)$_{1-6}$R$^{14}$;
Halogen, NO$_2$, CN, NHC

$R^{19}$ is alkyl having 1 to 20 carbon atoms,

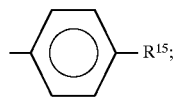

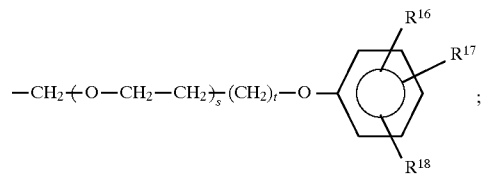

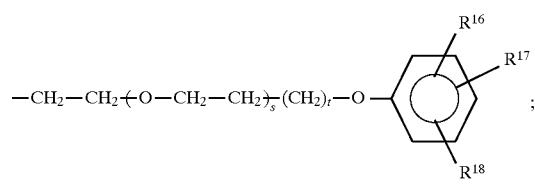

where s=0, 1 or 2
and t=0 or 1,
a five- or six-membered nitrogen-, oxygen- or sulfur-containing heteroaromatic radical, which is unsubstituted or substituted by alkyl having 1 to 22 carbon atoms,
O—$C_1$- to $C_{22}$-alkyl, S—$C_1$- to $C_{22}$-alkyl, NH—$C_1$- to $C_{22}$-alkyl
or

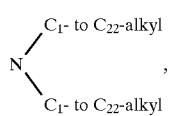

—C≡CH , —CH$_2$—C≡CH, —CH$_2$—C≡CH$_3$,
—CH$_2$—C≡C—C$_2$H$_5$, —CH$_2$ —CH$_2$—C≡CH,

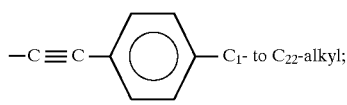 $C_1$- to $C_{22}$-alkyl;

and A is $-(CH_2)-_{4\ to\ 8}$, $-CH_2-O-CH_2-CH_2-OCH_2-$,
$-CH_2-O-CH_2-CH(CH_3)-O-CH_2-$,
$-CH_2-O-CH_2-CH_2-CH_2-O-CH_2-$,
$-CH_2-O-(CH_2)_4-O-CH_2-$,
$-O-(CH_2-CH_2-O)_{1\ or\ 2}$,
$-O-(CH_2-CH(CH_3)-O)_{1\ or\ 2}$ or

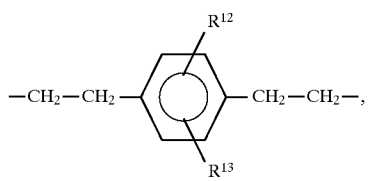

where $R^{12}$ and $R^{13}$, independently of one another, are as defined above or are halogen, CN, $NO_2$, $-N=N-R^{20}$ or

where $R^{20}$ is phenyl which is unsubstituted or substituted by $NO_2$, CN, halogen, $C_1$- to $C_4$-alkyl, $C_1$- to $C_4$-alkoxy, $C_1$- to $C_4$-alkylthio or $C_1$- to $C_4$-alkylamino, $R^{21}$ and $R^{22}$, independently of one another, are $C_1$- to $C_4$-alkyl, $C_1$- to $C_4$-alkoxy, CN, $NO_2$ or halogen,

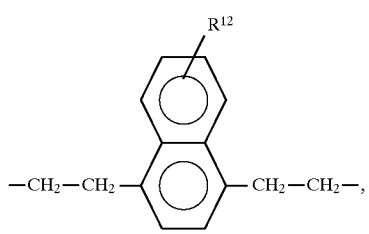

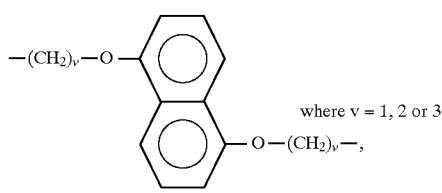

where v = 1, 2 or 3 or

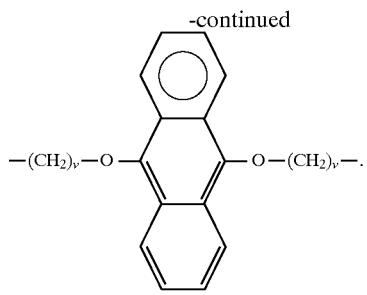

3. A compound as claimed in claim 1, wherein the axial-chiral groups linked to dendritic nitrogen-containing organic compounds of the formula (I) are those of the formula

[structure with $R^{24}$, CH=N—, OH, $R^{23}$] or

[naphthalene structure with CH=N—, OH, $R^{25}$]

where

=N— is in each case the nitrogen of the Schiff's base obtained from the primary amino group, $R^{23}$ and $R^{24}$, independently of one another, are $C_1$- to $C_{22}$-alkyl, $C_1$- to $C_6$-alkyloxy or phenyl which is unsubstituted or substituted by halogen, CN, $NO_2$, $C_1$- to $C_4$-alkyl or $C_1$- to $C_4$-alkoxy, or

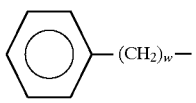

where w=1 to 4, with the proviso that at least one of $R^{23}$ and $R^{24}$ is tertbutyl or a radical which prevents the free 360° rotatability of the phenyl radicals, and $R^{25}$ is tert-butyl or phenyl which is unsubstituted or substituted by halogen, CN, $NO_2$, $C_1$- to $C_4$-alkyl or $C_1$- to $C_4$-alkoxy.

4. A compound as claimed in claim 2, in the form of a metal complex with a transition metal.

5. A compound as claimed in claim 3, in the form of a metal complex with a transition metal.

6. A process for the preparation of a dendritic, nitrogen-containing organic compound as claimed in claim 2 containing at least 4 planar-chiral groups, which comprises reacting a compound of the formula (I) as claimed in claim 1 with a hydroxyaldehyde of the formula

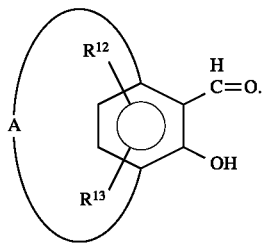

7. A process for the preparation of a dendritic, nitrogen-containing organic compound as claimed in claim 3 containing at least 4 axial-chiral groups, which comprises reacting a compound of the formula (I) as claimed in claim 1 with a hydroxyaldehyde of the formula

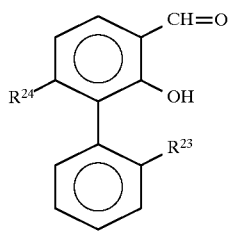

or

-continued

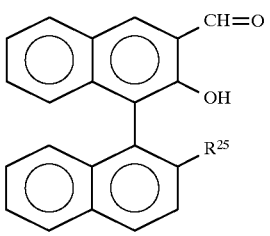

where $R^{23}$ to $R^{25}$ are as defined in claim 3.

8. A process for the preparation of a metal complex as claimed in claim 4, which comprises dissolving or dispersing a dendritic compound containing planar-chiral or axial-chiral groups together with a transition-metal salt in a suitable solvent at a temperature between room temperature and the boiling point of the solvent, subsequently removing the solvent, and freeing the resultant metal complex from excess metal salt by treatment with water.

9. A process for the preparation of a metal complex as claimed in claim 4, which comprises adding a transition-metal salt to the reaction mixture for the preparation of the Schiff's base.

10. A method for asymmetrical homogeneous catalysis wherein as catalyst a dendritic, nitrogen-containing organic compound as claimed in claim 1 is used.

11. A method for asymmetrical homogeneous catalysis wherein as catalyst a metal complex as claimed in claim 4 is used.

* * * * *

UNITED STATES PATENT AND TRADEMARK OFFICE
CERTIFICATE OF CORRECTION

PATENT NO.: 5,847,190

DATED: December 8, 1998

INVENTOR(S): PAULUS et al.

It is certified that error appears in the above-identified patent and that said Letters Patent is hereby corrected as shown below:

Col. 16, claim 1, line 14 bridging line 15, should be together as "--$(CH_2)_3$- --".

Col. 18, claim 2, line 23, delete "NHC".

Col. 19, claim 2, lines 16 and 17, the zeros "0" should be O's --O--.

Signed and Sealed this

Twenty-third Day of March, 1999

Attest:

Attesting Officer

Q. TODD DICKINSON

Acting Commissioner of Patents and Trademarks